(12) United States Patent
Darios et al.

(10) Patent No.: US 7,404,819 B1
(45) Date of Patent: Jul. 29, 2008

(54) IMPLANTABLE PROSTHESIS

(75) Inventors: Roger Darios, Foster, RI (US); Ronald L. Greene, Warwick, RI (US); Dennis Cherok, Harrisville, RI (US); Thomas J. Capuzziello, Milford, MA (US); James D. Mello, N. Dartmouth, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/661,623

(22) Filed: Sep. 14, 2000

(51) Int. Cl.
*A61B 17/08* (2006.01)
*A61F 2/02* (2006.01)

(52) U.S. Cl. .................. 606/151; 623/23.72; 623/23.76

(58) Field of Classification Search ............. 623/14.13, 623/11.11, 7, 8, 23.72, 23.71; 606/151; 600/37
See application file for complete search history.

(56) References Cited

U.S. PATENT DOCUMENTS

| | | | |
|---|---|---|---|
| 2,621,145 | A | 12/1952 | Sano |
| 2,671,444 | A | 3/1954 | Pease, Jr. |
| 3,054,406 | A | 9/1962 | Usher |
| 3,124,136 | A | 3/1964 | Usher |
| 3,272,204 | A | 9/1966 | Artandi et al. |
| 3,416,524 | A | 12/1968 | Meier |
| 3,625,209 | A | 12/1971 | Clark |
| 3,953,566 | A | 4/1976 | Gore |
| 3,965,703 | A | 6/1976 | Barnhardt |
| 4,051,848 | A | 10/1977 | Levine |
| 4,187,390 | A | 2/1980 | Gore |
| 4,277,429 | A | 7/1981 | Okita |

(Continued)

FOREIGN PATENT DOCUMENTS

CA 2114282 7/1994

(Continued)

OTHER PUBLICATIONS

Brown, M.D., Gregory L., et al., "Comparison of Prosthetic Materials for Abdominal Wall Reconstruction in the Presence of Contamination and Infections", Annals of Surgery, Jun. 1985, vol. 201, No. 6, pp. 705-711.

(Continued)

*Primary Examiner*—William H. Matthews
(74) *Attorney, Agent, or Firm*—Wolf Greenfield & Sacks, P.C.

(57) ABSTRACT

An implantable prosthesis and a method of repairing an anatomical defect, such as a tissue or muscle wall defect, by promoting tissue growth thereto, while limiting the incidence of postoperative adhesions between a portion of the prosthesis and tissue or organs. The prosthesis is formed of a biologically compatible, flexible layer of repair fabric suitable for reinforcing tissue or muscle and closing anatomical defects, and a barrier layer for physically isolating at least a portion of one side of the fabric from areas likely to form adhesions. A peripheral barrier extends about at least a portion of the outer peripheral edge of the repair fabric to inhibit adhesions between the outer peripheral edge and adjacent tissue and organs. The repair fabric may include an outer margin that has been melted and resolidified to render the outer peripheral edge substantially impervious to tissue ingrowth. The barrier layer may be joined to the repair fabric with connecting stitches formed from PTFE to inhibit the formation of adhesions thereto.

13 Claims, 4 Drawing Sheets

U.S. PATENT DOCUMENTS

| | | |
|---|---|---|
| 4,347,847 A | 9/1982 | Usher |
| 4,400,833 A | 8/1983 | Kurland |
| 4,403,604 A | 9/1983 | Wilkinson et al. |
| 4,452,245 A | 6/1984 | Usher |
| 4,478,665 A | 10/1984 | Hubis |
| 4,561,434 A | 12/1985 | Taylor |
| 4,576,608 A | 3/1986 | Homsy |
| 4,585,458 A | 4/1986 | Kurland |
| 4,633,873 A | 1/1987 | Dumican et al. |
| 4,655,221 A | 4/1987 | Devereux |
| 4,693,720 A | 9/1987 | Scharnberg et al. |
| 4,713,075 A | 12/1987 | Kurland |
| 4,725,279 A | 2/1988 | Woodroof |
| 4,760,102 A | 7/1988 | Moriyama et al. |
| 4,769,038 A | 9/1988 | Bendavid et al. |
| 4,796,603 A | 1/1989 | Dahlke et al. |
| 4,840,626 A | 6/1989 | Linsky et al. |
| 4,854,316 A | 8/1989 | Davis |
| 4,865,026 A | 9/1989 | Barrett |
| 4,871,365 A | 10/1989 | Dumican |
| 4,882,162 A | 11/1989 | Ikada et al. |
| 4,942,875 A | 7/1990 | Hlavacek et al. |
| 4,955,907 A | 9/1990 | Ledergerber |
| 4,994,084 A | 2/1991 | Brennan |
| 4,997,440 A | 3/1991 | Dumican |
| 5,002,551 A | 3/1991 | Linsky et al. |
| 5,007,916 A | 4/1991 | Linsky et al. |
| 5,092,884 A | 3/1992 | Devereux et al. |
| 5,100,422 A | 3/1992 | Berguer et al. |
| 5,104,400 A | 4/1992 | Berguer et al. |
| 5,110,527 A | 5/1992 | Harada et al. |
| 5,116,357 A | 5/1992 | Eberbach |
| 5,116,360 A | 5/1992 | Pinchuk et al. |
| 5,122,155 A | 6/1992 | Eberbach |
| 5,141,515 A | 8/1992 | Eberbach |
| 5,141,522 A | 8/1992 | Landi |
| 5,147,374 A | 9/1992 | Fernandez |
| 5,147,401 A | 9/1992 | Bakker et al. |
| 5,195,542 A | 3/1993 | Gazielly et al. |
| 5,201,745 A | 4/1993 | Tayot et al. |
| 5,217,494 A | 6/1993 | Coggins et al. |
| 5,222,987 A | 6/1993 | Jones |
| 5,234,739 A | 8/1993 | Tanaru et al. |
| 5,234,751 A | 8/1993 | Harada et al. |
| 5,254,133 A | 10/1993 | Seid |
| 5,258,000 A | 11/1993 | Gianturco |
| 5,282,851 A | 2/1994 | Jacob-LaBarre |
| 5,290,217 A | 3/1994 | Campos |
| 5,292,328 A | 3/1994 | Hain et al. |
| 5,326,355 A | 7/1994 | Landi |
| 5,333,624 A | 8/1994 | Tovey |
| 5,334,217 A | 8/1994 | Das |
| 5,350,388 A | 9/1994 | Epstein |
| 5,356,432 A | 10/1994 | Rutkow et al. |
| 5,366,460 A | 11/1994 | Eberbach |
| 5,368,602 A | 11/1994 | de la Torre |
| 5,370,650 A | 12/1994 | Tovey et al. |
| 5,379,754 A | 1/1995 | Tovey et al. |
| 5,425,740 A | 6/1995 | Hutchinson, Jr. |
| 5,433,996 A | 7/1995 | Kranzler et al. |
| 5,451,235 A | 9/1995 | Lock et al. |
| 5,456,720 A | 10/1995 | Schultz et al. |
| 5,461,885 A | 10/1995 | Yokoyama et al. |
| 5,480,436 A | 1/1996 | Bakker et al. |
| 5,507,811 A | 4/1996 | Koike et al. |
| 5,508,036 A | 4/1996 | Bakker et al. |
| 5,519,004 A | 5/1996 | Urry |
| 5,522,896 A | 6/1996 | Prescott |
| 5,524,633 A | 6/1996 | Heaven et al. |
| 5,545,178 A | 8/1996 | Kensey et al. |
| 5,569,273 A | 10/1996 | Titone |
| 5,591,234 A | 1/1997 | Kirsch |
| 5,593,441 A | 1/1997 | Lichtenstein et al. |
| 5,601,579 A | 2/1997 | Semertzides |
| 5,614,284 A | 3/1997 | Kranzler et al. |
| 5,634,931 A | 6/1997 | Kugel |
| 5,634,944 A | 6/1997 | Magram |
| 5,653,760 A | 8/1997 | Saffran |
| 5,686,090 A | 11/1997 | Schilder et al. |
| 5,695,525 A | 12/1997 | Mulhauser et al. |
| 5,697,978 A | 12/1997 | Sgro |
| 5,716,408 A | 2/1998 | Eldridge et al. |
| 5,716,409 A | 2/1998 | Debbas |
| 5,722,992 A | 3/1998 | Goldman |
| 5,725,577 A | 3/1998 | Saxon |
| 5,733,337 A | 3/1998 | Carr, Jr. et al. |
| 5,743,917 A | 4/1998 | Saxon |
| 5,759,204 A | 6/1998 | Seare, Jr. |
| 5,766,246 A | 6/1998 | Mulhauser et al. |
| 5,769,864 A | 6/1998 | Kugel |
| 5,795,584 A | 8/1998 | Totakura et al. |
| 5,813,975 A | 9/1998 | Valenti |
| 5,824,082 A | 10/1998 | Brown |
| 5,855,613 A | 1/1999 | Antanavich et al. |
| 5,861,034 A | 1/1999 | Taira et al. |
| 5,879,366 A | 3/1999 | Shaw et al. |
| 5,916,225 A | 6/1999 | Kugel |
| 5,919,232 A | 7/1999 | Chaffringeon et al. |
| 5,922,026 A | 7/1999 | Chin |
| 5,948,020 A | 9/1999 | Yoon et al. |
| 5,954,767 A | 9/1999 | Pajotin et al. |
| 5,972,007 A | 10/1999 | Sheffield et al. |
| 5,990,378 A | 11/1999 | Ellis |
| 5,990,380 A | 11/1999 | Marotta et al. |
| 6,004,333 A | 12/1999 | Sheffield et al. |
| 6,015,844 A | 1/2000 | Harvey et al. |
| 6,031,148 A | 2/2000 | Hayes et al. |
| 6,066,776 A | 5/2000 | Goodwin et al. |
| 6,066,777 A | 5/2000 | Benchetrit |
| 6,075,180 A * | 6/2000 | Sharber et al. ............ 606/76 |
| 6,113,623 A | 9/2000 | Sgro |
| 6,120,539 A | 9/2000 | Eldridge et al. |
| 6,174,320 B1 | 1/2001 | Kugel et al. |
| 6,224,616 B1 | 5/2001 | Kugel |
| 6,258,124 B1 | 7/2001 | Darois et al. |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,280,453 B1 | 8/2001 | Kugel et al. |
| 6,290,708 B1 | 9/2001 | Kugel et al. |
| 6,319,264 B1 | 11/2001 | Tormala et al. |
| 6,368,541 B1 * | 4/2002 | Pajotin et al. ............ 264/324 |
| 6,383,201 B1 | 5/2002 | Dong |
| 6,451,032 B1 | 9/2002 | Ory et al. |
| 6,497,650 B1 | 12/2002 | Nicolo |
| 6,565,580 B1 | 5/2003 | Beretta |
| 6,652,595 B1 | 11/2003 | Nicolo |
| 7,156,804 B2 | 1/2007 | Nicolo |

FOREIGN PATENT DOCUMENTS

| | | |
|---|---|---|
| DE | 298 17 682 U1 | 3/1999 |
| EP | 0 194 192.3 A1 | 9/1986 |
| EP | 0 334 046 A2 | 9/1989 |
| EP | 0 358 819 A1 | 3/1990 |
| EP | 0 362 113 A1 | 4/1990 |
| EP | 0474887 A1 | 10/1991 |
| EP | 0 560 934 B2 | 9/1993 |
| EP | 0 692 225 A | 1/1996 |
| EP | 0 719 527 A1 | 7/1996 |
| EP | 0 827 724 A2 | 3/1998 |
| EP | 0 537 769 | 4/1998 |
| FR | 2145975 | 2/1973 |
| FR | 2 744 906 A1 | 8/1997 |

| | | |
|---|---|---|
| FR | 2 766 716 | 2/1999 |
| GB | 1 352 282 | 5/1974 |
| GB | 1 406 271 | 9/1975 |
| SU | 1718857 A1 | 3/1992 |
| WO | WO 82/04390 A1 | 12/1982 |
| WO | WO 90/14796 A1 | 12/1990 |
| WO | WO 92/10218 A1 | 6/1992 |
| WO | WO 92/19162 A2 | 11/1992 |
| WO | WO 93/17635 A1 | 9/1993 |
| WO | WO 94/17747 A1 | 8/1994 |
| WO | WO 94/19029 A1 | 9/1994 |
| WO | WO 94/27535 A1 | 12/1994 |
| WO | WO 96/09795 A1 | 4/1996 |
| WO | WO 96/14805 A1 | 5/1996 |
| WO | WO 96/40307 | 12/1996 |
| WO | WO 97/21461 A1 | 6/1997 |
| WO | WO 97/35533 A1 | 10/1997 |
| WO | WO 98/14134 A2 | 4/1998 |
| WO | WO 98/49967 A | 11/1998 |
| WO | WO 99/06079 A1 | 2/1999 |
| WO | WO 99/51163 A1 | 10/1999 |
| WO | WO 00/07520 A1 | 2/2000 |
| WO | WO 00/16822 | 3/2000 |
| WO | WO 01/08594 A | 2/2001 |
| WO | WO 01/54589 | 2/2001 |
| WO | WO 01/43789 A1 | 6/2001 |
| WO | WO 01/85060 A1 | 11/2001 |
| WO | 1 317 227 B1 | 11/2004 |

OTHER PUBLICATIONS

Cardona, Hernando M.D., "Prosthokeroplasty", Cornea, 1983, vol. 2, No. 3, pp. 179-182.

Interceed(TC7) Adhesion Barrier Study Group (Cohen, Stephen M., et al.), "Prevention of postsurgical adhesions by Interceed(TC7),*an absorbable adhesion barrier: a prospective, randomized multicenter clinical study", Fertility and Sterility, Jun. 1989, vol. 51, No. 6, .pp. 933-938.

Jenkins, Scott D., M.D., et al., A Comparison of Prosthetic Materials Used to Repair Abdominal Wall Defects, Surgery, Aug. 1983, vol. 94, No. 2, pp. 392-398.

Uzzo, Robert G. et al., "The Effects of Mesh Bioprosthesis on the Spermatic Cord Structures: A Preliminary Report in a Canine Model", The Journal Of Urology, Apr. 1999, vol. 161, pp. 1344-1349.

Walker, Alonzo P., M.D., et al., "Double-Layer Prostheses for Repair of Abdominal Wall Defects in a Rabbit Model.", Jun. 1992, vol. 55, No. 1, pp. 32-37.

Bard, http://www.davol.com/max.htm, Bard® 3DMax™ Mesh, 2 pages, printed Sep. 10, 2002.

Goldstein, Harold, M.D., F.A.C.S.; atrium Polypropylene Mesh, "An Atlas of Hernia Repair Using an Inguinal Hernia Repair Preshape with Keyhole Slit", Atrium Medical Corporation, Jun. 1995, 5 pp.

Groupe Floreane Medical Implants; Reference document 2002-2003; http://www.actusnews.fr/documents/ACTUS-0-664-041118_doc_de_ref_2002_2003.pdf.

Jarsaillon, P., Hernia (2000) 4 [Suppl.]: S17-S21; Case Reports: Laparoscopic treatment of an umbilical hernia using a new composite mesh; (c) Springer-Verlag 2000.

Parviz K. Amid et al., "Experimental evaluation of a new composite mesh with the selective property of incorporation to the abdominal wall without adhering to the intestines", Journal of Biomedical Materials Research, vol. 28, 373-375 (1994).

Sofradim International, Parietex® Composite, company brochure; (4) pages.

B.G. Matapurkar et al., "A New Technique of "Marlex®-Peritoneal Sandwich" in Repair of Large Incisional Hernias", World Journal of Surgery 15, 768-770, 1991.

M. L. Baptista, et al. "Abdominal Adhesions to Prosthetic Mesh Evaluated by Laparoscopy and Electron Microscopy", Journal of the American College of Surgeons, Mar. 2000.

Woodward et al., "The Tissue Response to Implants and Its Evaluation by Light Microscopy", Handbook of Biomaterials Evaluation, MacMillan Publishing Company, 364-378, 1986.

Boyers et al., "Reduction of postoperative pelvic adhesions in the rabbit with Gore-Tex surgical membrane", Fertility and Sterility, vol. 49 No. 6, 1066-1070, Jun. 1988.

European Search Report for European Application EP 07 11 3064.

* cited by examiner

IMPLANTABLE PROSTHESIS

FIELD OF INVENTION

The present invention relates to an implantable prosthesis and, more particularly, to a composite prosthesis for use in soft tissue repair and reconstruction that limits the incidence of postoperative adhesions.

DISCUSSION OF RELATED ART

Various prosthetic materials have been proposed to repair and reinforce anatomical defects, such as tissue and muscle wall hernias. For example, ventral and inguinal hernias are commonly repaired using a sheet of biocompatible fabric, such as a knitted polypropylene mesh (BARD MESH). The fabric is typically sutured, stapled or otherwise provisionally anchored in place over, under or within the defect. Tissue integration with the fabric, such as by tissue ingrowth into and/or along the fabric, eventually completes the repair.

It has been suggested that in certain procedures, the prosthetic fabric may come into contact with tissue or organs potentially leading to undesirable postoperative adhesions between the mesh and the tissue or organs. It had been proposed in U.S. Pat. No. 5,593,441, assigned to C.R. Bard, Inc., also the assignee of the present application, to repair ventral hernias and/or reconstruct chest walls using a prosthesis that is covered with an adhesion resistant barrier, such as a sheet of expanded PTFE. In the repair of ventral hernias, the composite is positioned with the barrier facing the region of potential adhesion, such as the abdominal viscera, and in the case of chest wall reconstruction, the barrier faces the thoracic viscera (i.e., heart and lungs). Other configurations of composite prostheses can be found in U.S. Pat. Nos. 5,695,525; 5,725,577 and 5,743,917, each of which is also assigned to C.R Bard, Inc.

International Publication No. WO 97/35533, also assigned to C.R. Bard, Inc., proposed a universal composite prosthesis in which one side of a layer of mesh material is covered with a layer of barrier material. The mesh material promotes biological tissue ingrowth while the barrier material retards biological tissue adherence thereto. The prosthesis may be utilized for various surgical procedures, including ventral hernia repair and inguinal hernia repair.

It is an object of the present invention to provide an improved method and prosthesis for the repair of tissue and muscle wall defects.

SUMMARY OF THE INVENTION

The present invention is an implantable prosthesis and a method of repairing an anatomical defect, such as a tissue or muscle wall defect, by promoting tissue growth thereto, while limiting the incidence of postoperative adhesions between a portion of the prosthesis and tissue or organs. The prosthesis is formed of a biologically compatible, flexible layer of repair fabric suitable for reinforcing tissue or muscle and closing anatomical defects, and a barrier layer for physically isolating at least a portion of one side of the fabric from areas likely to form adhesions.

In one embodiment of the invention, a peripheral barrier extends about at least a portion of an outer peripheral edge of the repair fabric to inhibit adhesions between the outer peripheral edge and adjacent tissue and organs.

According to one aspect of the invention, the peripheral barrier may be formed integral with the repair fabric. More particularly, a portion of the outer margin of the repair fabric may be melted and resolidified to render an outer peripheral edge that is substantially impervious to tissue ingrowth.

In another aspect of the invention, the peripheral barrier may be formed integral with the barrier layer. More particularly, a portion of the outer margin of the barrier layer may be wrapped about an outer peripheral edge of the repair fabric.

According to a further aspect of the invention, the peripheral barrier may be a separate component that is disposed along the outer peripheral edge of the repair fabric. In this regard, adhesion resistant material may be provided about the outer peripheral edge of the repair fabric. Additionally, or alternatively, the material may be impregnated into or otherwise attached to the fabric.

In another embodiment of the invention, the layer of repair fabric includes an inner body and an outer margin extending from the inner body, the outer margin including an outer peripheral edge. Each of the inner body and the outer peripheral edge has a thickness with the thickness of the outer peripheral edge being less than the thickness of the inner body.

In a further embodiment of the invention, the layer of repair fabric includes an outer margin with an outer peripheral edge that has been melted and resolidified to render the outer peripheral edge resistant to the formation of adhesions with tissue and organs.

In still another embodiment of the invention, a plurality of connecting stitches joins the barrier layer to the portion of the repair fabric, the plurality of connecting stitches being formed from PTFE to inhibit the formation of adhesions thereto.

In still a further embodiment of the invention, the layer of repair fabric includes an outer margin with an outer peripheral edge, the outer margin being reinforced to form a bite region for securing the prosthesis along the outer margin.

Other objects and features of the present invention will become apparent from the following detailed description when taken in connection with the accompanying drawings. It is to be understood that the drawings are designed for the purpose of illustration only and are not intended as a definition of the limits of the invention.

BRIEF DESCRIPTION OF THE DRAWINGS

The foregoing and other objects and advantages of the invention will be appreciated more fully from the following drawings, wherein like reference characters designate like features, in which.

DESCRIPTION OF ILLUSTRATIVE EMBODIMENTS

Figure 1:
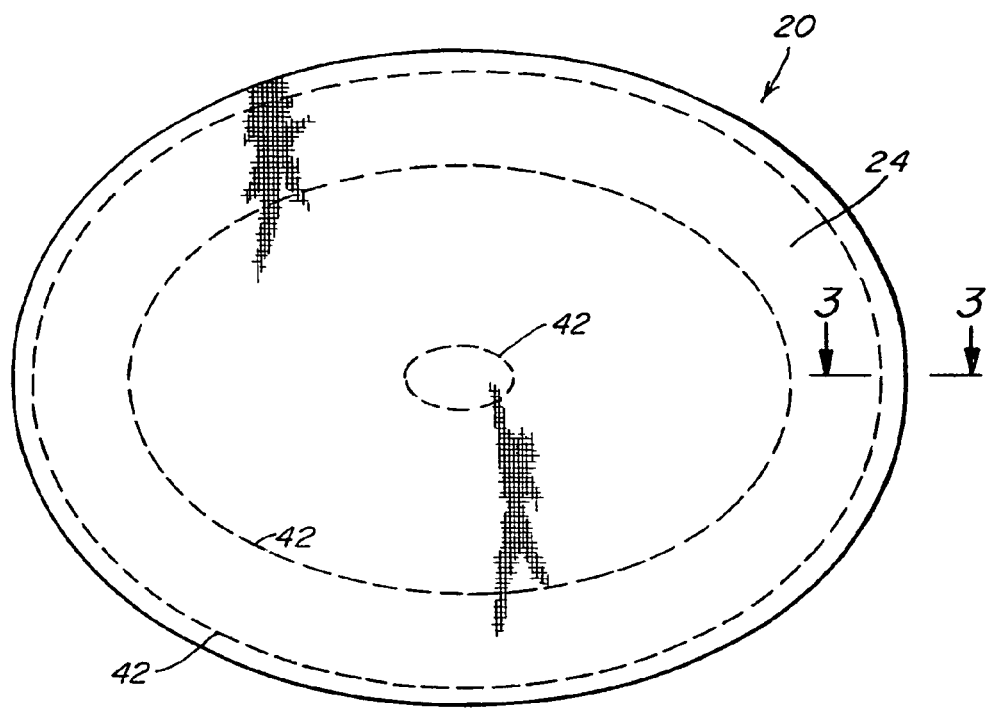
FIG. 1 is a top plan view of an implantable prosthesis in accordance with one illustrative embodiment of the present invention.
Figure 2:
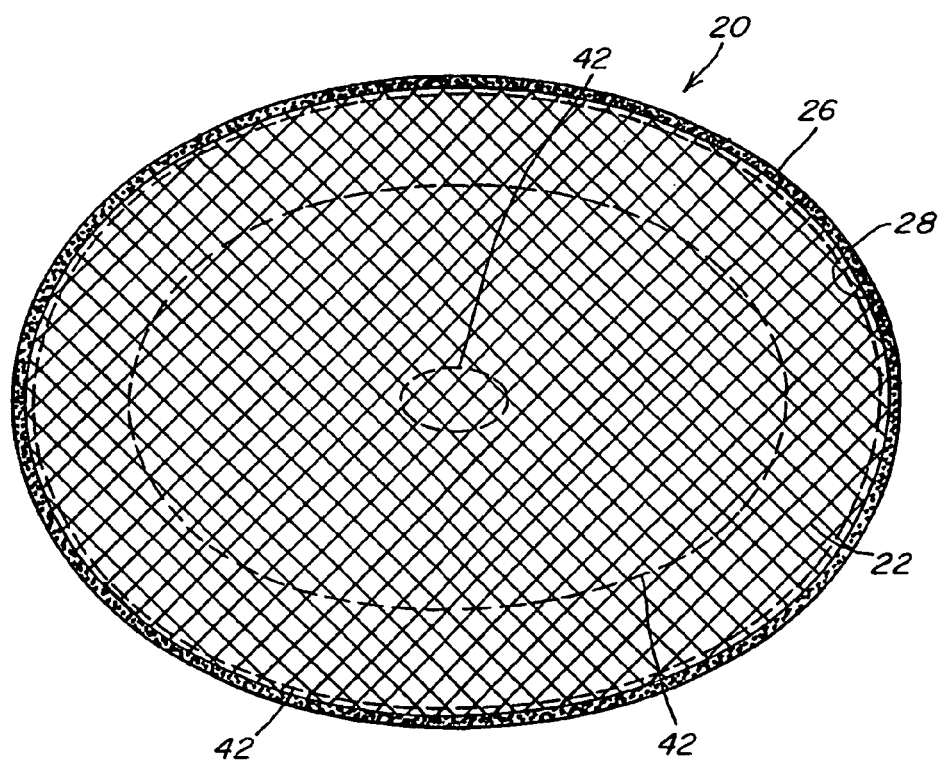
FIG. 2 is a bottom plan view of the prosthesis of FIG. 1.
Figure 3:
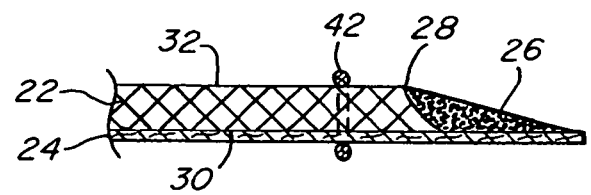
FIG. 3 is a cross-sectional view of the outer margin of the prosthesis taken along section line 3-3 of FIG. 1.

FIGS. 1-3 illustrate one embodiment of an implantable prosthesis for repairing soft tissue and wall defects, such as ventral and inguinal hernias, and/or for chest wall reconstruction by promoting tissue ingrowth thereto while limiting the incidence of postoperative adhesions to selected portions of the prosthesis. The prosthesis 20 includes a layer of tissue infiltratable repair fabric 22, an adhesion resistant barrier layer 24 overlying at least a portion of one side of the fabric, and a peripheral barrier 26 extending about a portion of the outer peripheral edge 28 of the fabric.

The repair fabric 22 is formed of a biologically compatible, flexible material that includes a plurality of interstices or openings which allow sufficient tissue ingrowth to secure the prosthesis to host tissue after implantation. The barrier layer 24 and the peripheral barrier 26 are formed of a material and/or with a structure that does not substantially stimulate tissue ingrowth and adhesion formation when implanted in tissue to limit the incidence of postoperative tissue adhesions between the fabric and adjacent tissue and organs.

The prosthesis 20 may be relatively flat and sufficiently pliable to allow a surgeon to manipulate the shape of the implant to conform to the anatomical site of interest and to be sutured or stapled thereto. The shape and size of the composite implant, and of the respective repair fabric 22, barrier layer 24 and peripheral barrier 26, may vary according to the surgical application as would be apparent to one of skill in the art. In this regard, it is contemplated that the prosthesis may be preshaped or shaped by the surgeon during the surgical procedure. It is also contemplated that two or more sheets of fabric and/or barrier material may be implemented in one or more layers of the prosthesis. The layers may have the same size and shape, or may have a different size and/or shape. A separate layer of material may be employed between the repair fabric and the barrier layer. The prosthesis also may have a plug or three-dimensional shape, with selected portions, or all of, the edges of the plug covered by barrier material.

As illustrated, the barrier layer 24 may cover the entire surface of a first side 30 of the repair fabric 22. This particular configuration allows tissue ingrowth to a second side 32 of the repair fabric while inhibiting adhesions to tissue and organs located opposite the anatomical defect site. It is to be appreciated, however, that the barrier layer 24 may be configured to cover only selected portions of the first side of the fabric 22 to enhance tissue ingrowth from both sides of the fabric in those portions free of the barrier layer.

In some instances, it may be desirable to isolate the outer peripheral edge of the repair fabric from adjacent tissue and organs. In the illustrative embodiment, the peripheral barrier 26 extends completely about the outer peripheral edge 28 of the fabric to inhibit adhesions thereto. It is to be understood, however, that the peripheral barrier 26 may be configured to cover only selected portions of the outer peripheral edge of the fabric that one may wish to protect from the formation of postoperative adhesions, such as portions of the edge that may be exposed to tissue and organs.

The peripheral barrier 26 may be formed integral with either the repair fabric 22 or the barrier layer 24. Alternatively, the peripheral barrier 26 may be formed by a separate component that is attached to or incorporated into the outer peripheral edge of the implant.

In one illustrative embodiment shown in FIGS. 1-3, the peripheral barrier 26 is formed from a portion of the repair fabric 22. In particular, the repair fabric 22 may be altered so as to substantially eliminate the tissue infiltratable interstices or openings along its outer margin, thereby creating a peripheral barrier 26 which inhibits tissue ingrowth to the outer peripheral edge 28 of the fabric.

In one embodiment, the outer margin of the repair fabric 22 is melted to seal the fabric material and form an outer peripheral barrier 26. The barrier layer 24 may be configured, such as with submicronal sized pores, so that a portion of the melted fabric material becomes fused to the barrier layer 24. In this arrangement, the peripheral barrier 26 may act to increase the stiffness of the outer margin of the barrier layer, such that the outer edge of the barrier layer may become more resistant to being inadvertently folded back. Additionally, the outer margin of the barrier layer may tend to soften and thereby reduce the brittleness of the peripheral barrier. The outer peripheral barrier may have a width that is approximately equal to or greater than the thickness of the fabric material.

The outer margin of the fabric 22 may be melted using any suitable process as would be apparent to one of skill in the art. In one embodiment, the outer margin may be melted by heat sealing the fabric. Other processes may include ultrasonic, induction, vibration, infrared/laser welding and the like.

As shown in FIG. 3, the peripheral barrier 26 may be configured to decrease in thickness in an outward direction away from the outer peripheral edge 28 of the repair fabric and toward the outer edge of the barrier layer 24. In one embodiment, the peripheral barrier 26 has a tapered shape resulting in a low profile edge relative to the rest of the prosthesis that may enhance the adhesion resistance of the peripheral barrier 26. The tapered shape may also provide the prosthesis with a relatively flexible, adhesion resistant outer margin. It is to be understood, however, that any suitable shape may be employed for the peripheral barrier as would be recognized by one of skill in the art. For example, the peripheral barrier 26 may be formed with a stepped configuration, with a non-uniform taper, or with a constant thickness.

Figure 6:
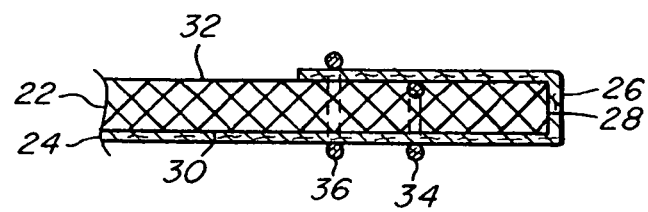
FIG. 6 is a cross-sectional view of the outer margin of the prosthesis taken along section line 6-6 of FIG. 4.
Figure 4:
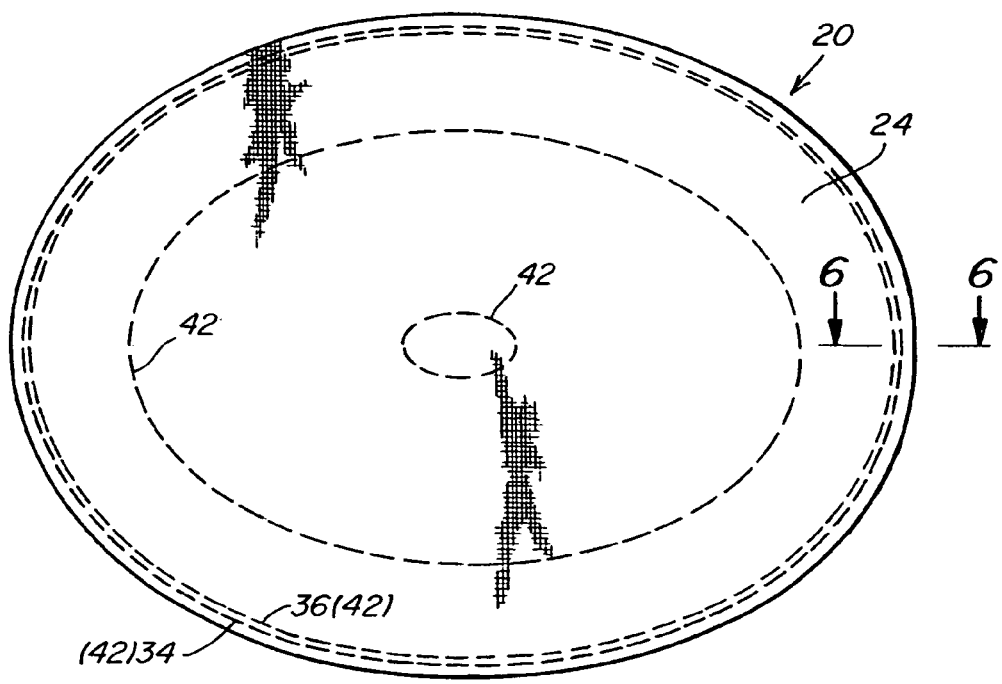
FIG. 4 is a top plan view of an implantable prosthesis in accordance with another illustrative embodiment of the present invention.
Figure 5:
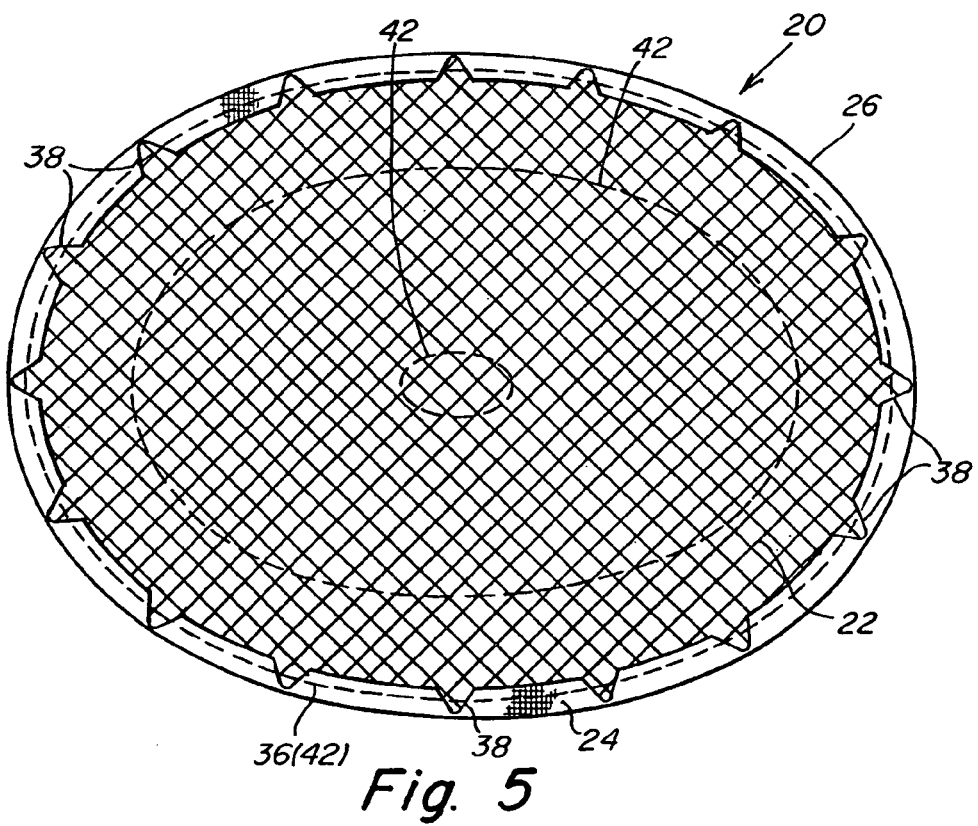
FIG. 5 is a bottom plan view of the prosthesis of FIG. 4.

In another illustrative embodiment shown in FIGS. 4-6, the peripheral barrier 26 is formed from a portion of the barrier layer 24. In particular, the outer margin of the barrier layer may be extended along a portion of the layer of repair fabric 22 so that it covers at least a portion of the outer peripheral edge 28 of the fabric.

In one embodiment, the outer margin of the barrier layer 24 is wrapped about the repair fabric 22 so that it extends from the first side 30 of the repair fabric and across the thickness of the outer peripheral edge 28 of the fabric. The barrier layer 24 may further extend inwardly across a portion of the second side 32 of the fabric adjacent the outer peripheral edge 28. The barrier material may be hemmed about the repair fabric and secured with stitches 34, 36 placed inward of the outer peripheral edge of the fabric. This configuration essentially encapsulates the outer peripheral edge of the fabric with barrier material to inhibit adhesions thereto.

The barrier material, however, does not need to wrap around the peripheral edge and across the second side of the fabric as shown in FIG. 6. In this regard, the barrier material may extend across and be joined to the outer peripheral edge of the fabric. For example, the barrier material may be bonded to the outer peripheral edge of the fabric with any suitable adhesive, such as a silicone, that is compatible with the particular fabric and barrier materials.

Figure 7:
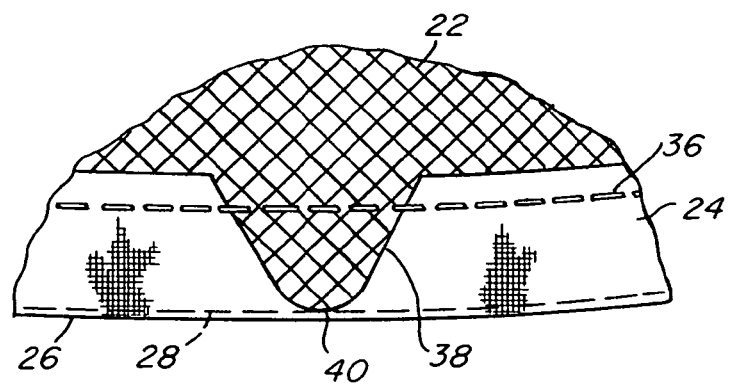
FIG. 7 is a fragmented view of the outer margin of the prosthesis of FIG. 5.

It may be desirable to configure the hemmed portion of the prosthesis with fluid drainage so as to reduce the potential for entrapping fluid along its outer margin that could lead to a seroma and/or an infection. In one illustrative embodiment shown in FIGS. 5 and 7, the portion of the barrier layer 24 overlying the second side 32 of the repair fabric 22 includes a plurality of apertures 38 adjacent the outer peripheral edge 28 of the fabric. The apertures 38 should have a sufficient size and be located to permit fluid drainage. In this regard, the apertures 38 may be spaced inwardly and slightly away from the outer peripheral edge 28 of the fabric, as shown in the figures.

In one embodiment, the apertures 38 may include slits that extend inwardly away from the peripheral edge 28 of the fabric. As shown, the slits may have a generally V-shape that not only allows fluid drainage, but also reduces the likelihood of developing wrinkles or puckers along the outer margin of the prosthesis as the barrier layer is wrapped about the peripheral edge of the fabric. This may be of particular concern when the prosthesis has a curved configuration as shown. In one embodiment, the apex 40 of the apertures 38 may be spaced inwardly approximately 0.020 to 0.030 inches from the outer peripheral edge 28 of the fabric. Of course, one of skill in the art would readily recognize that any suitable aperture configuration may be employed to provide fluid drainage and/or reduce wrinkle development along the outer margin of the prosthesis. For example, the apertures 38 may be configured as a pattern of holes distributed on the portion of the barrier layer overlying the second side of the fabric. In one embodiment, the apertures may have a diameter of approximately 1 mm that may be spaced approximately 5 mm apart.

The repair fabric 22 and barrier layer 24 may be configured to have any suitable shape that is conducive to facilitating the repair of a particular defect. In the embodiments illustrated in FIGS. 1-6, the prosthesis 20 has a generally elliptical or oval shape. Examples of other shapes include, but are not limited to, circular, square and rectangular shapes.

In one embodiment, the repair fabric 22 is formed of a sheet of knitted polypropylene monofilament mesh fabric such as BARD MESH available from C.R. Bard, Inc. When implanted, the polypropylene mesh promotes rapid tissue ingrowth into and around the mesh structure. Alternatively, other surgical materials which are suitable for tissue reinforcement and defect closure may be utilized including PROLENE, SOFT TISSUE PATCH (microporous ePTFE), SURGIPRO, TRELEX, ATRIUM and MERSELENE. Absorbable materials, including polyglactin (VICRYL) and polyglycolic acid (DEXON), may be suitable for applications involving temporary repair of tissue or wall defects. It also is contemplated that the mesh fabric may be formed from multifilament yarns and that any suitable method, such as knitting, weaving, braiding, molding and the like, may be employed to form the prosthetic mesh material.

In one embodiment, the barrier layer 24 is formed from a sheet of expanded polytetrafluoroethylene (ePTFE) having a pore size (submicronal) that discourages tissue ingrowth and adhesion. Examples of suitable material include FLUORO-TEX Pericardial and Peritoneum Surgical Membrane and FLUORO-TEX Dura Substitute available from C.R. Bard and PRECLUDE Pericardial Membrane, PRECLUDE Peritoneal Membrane and PRECLUDE Dura Substitute membrane available from W.L. Gore & Associates, Inc. A representative and non-limiting sampling of other suitable non-porous materials includes silicone elastomer, such as SILASTIC Rx Medical Grade Sheeting (Platinum Cured) distributed by Dow Corning Corporation, TEFLON mesh, and microporous polypropylene sheeting (CELGARD) and film. Autogenous, heterogenous and xenogeneic tissue also are contemplated including, for example, pericardium and small intestine submucosa. Absorbable materials, such as SEPRAFILM available from Genzyme Corporation and oxidized, regenerated cellulose (Intercede (TC7)) may be employed for some applications. It is to be appreciated that any suitable adhesion resistant materials may be used as would be apparent to one of skill in the art.

In the illustrative embodiments described above, the repair fabric 22 and the barrier layer 24 are integrally connected with one or more connecting stitches 42. As shown in FIGS. 1 and 4, multiple series of stitches 42 (including hem stitches 34, 36) may be formed in a concentric pattern that follows the shape of the prosthesis. Stitching may allow total tissue infiltration to the fabric while providing a strong connection between the fabric and the barrier layer. The concentric pattern also maintains composite integrity by preventing the barrier 24 and underlying fabric 22 from separating should the prosthesis be trimmed by the surgeon to match a particular size and shape of the repair site. Any suitable pattern, however, may be employed so as to minimize separation of the fabric and the barrier layer.

In one embodiment, the stitches 42 (including hem stitches 34, 36) are formed with a polytetrafluoroethylene (PTFE) monofilament. PTFE stitches may provide a softer, more flexible prosthesis that is easier to manipulate as compared to a prosthesis using other stitch materials, such as polypropylene monofilament. PTFE monofilament also facilitates the manufacturing process due to the low friction characteristics of the material. Additionally, PTFE stitches may tend to be more adhesion resistant than other materials. Nevertheless, it should be understood that any suitable material, such as polypropylene monofilament, may be employed for the stitches.

The barrier layer 24 may be stitched to the repair fabric 22 by positioning the barrier material on the fabric to face the sewing needle so that the locking portion of each stitch is formed on the fabric side of the composite rather than on the barrier side to reduce the incidence of localized adhesions with tissue and organs. The stitches may be formed using a #10 ball-tipped needle to reduce the potential incidence of tissue ingrowth through the stitch holes. The sheets of fabric and barrier material may be held by a frame during the sewing procedure on a computer controlled table that has been programmed with the desired stitch pattern.

Any other suitable fastening technique and material may be employed to attach the barrier layer 24 to the repair fabric 22. For example, the barrier layer 24 may be bonded to the fabric 22 using an adhesive dispensed in a desired pattern, such as a spiral pattern, a serpentine pattern or a grid-like pattern of dots or beads, that maintains a sufficient quantity of open or non-impregnated interstices for tissue infiltration. Alternatively, the barrier layer 24 may be laminated or heat fused to the fabric 22 by a combination of heat and pressure. This lamination technique may be enhanced by a second layer of fabric such as is described in U.S. Pat. No. 6,120,539 which is also assigned to C.R. Bard, Inc., the assignee of the present application, and is incorporated herein by reference. The barrier may also be insert molded to the fabric using any suitable molding process.

It may be desirable to reinforce the outer margin of the prosthesis 20, particularly when the prosthesis may be secured using fasteners, such as sutures, staples and the like, along its outer margin. In one illustrative embodiment, a stitch line 42 (FIG. 3) and 36 (FIG. 6) is provided along the circumference of the prosthesis slightly inward of the peripheral barrier 26 to form a bite region away from the outer peripheral edge 28 of the fabric that is configured to receive a fastener for securing the prosthesis along its circumference. In this regard, a fastener, such as a suture, may be attached to the prosthesis inward of the stitch line 42 so that the stitch line may resist tension placed on the suture. In one embodiment, the stitch line may be located approximately 3 mm inward from the outer peripheral edge 28 to form a bite region having a width of approximately 4 mm. Of course, any suitable reinforcement configuration apparent to one of skill may be employed along the outer margin of the prosthesis.

In an exemplary embodiment, the composite prosthesis 20 includes an approximately 0.027 inch thick sheet 22 of BARD MESH knitted from polypropylene monofilament with a diameter of approximately 0.006 inches. An approximately 0.006 to 0.008 inch thick sheet 24 of ePTFE is attached to the mesh using approximately 3 mm to 4 mm long stitches 42 formed of a 0.008 inch to 0.012 inch diameter PTFE monofilament. The prosthesis 20 has a generally elliptical shape that may be configured to have any desired size. The peripheral barrier 26 has a width of approximately 0.10 inches with a tapered shape having a thickness of approximately 0.005 inches at its tip. It should be understood, however, that these dimensions are merely exemplary and that any suitable sizes and shapes may be employed for the prosthesis.

In the exemplary embodiment, the peripheral barrier 26 is formed by melting a ring of polypropylene mesh fabric 22 to the ePTFE barrier layer 24 in a generally elliptical shape that approximates the desired configuration of the prosthesis. This may be accomplished by overlying oversized sheets of the mesh fabric and ePTFE material in a fixture and heat sealing the layers using a heated die configured with the desired shape of the prosthesis. The melted ring may be formed by applying heat to the fabric at a temperature range of approximately 320° F. to 400° F. for a period of approximately 3 to 5 seconds. Once fused, the fabric and barrier layer are stitched, as described above, and subsequently die cut flush along a portion of the ring to complete the prosthesis with a peripheral barrier.

Figure 8:
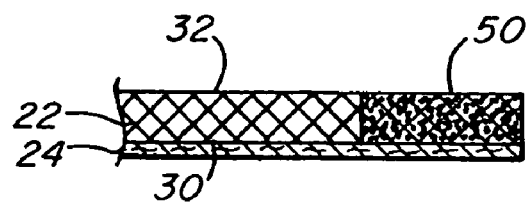
FIG. 8 is a cross-sectional view of the outer margin of a prosthesis in accordance with another illustrative embodiment of the present invention.
Figure 9:
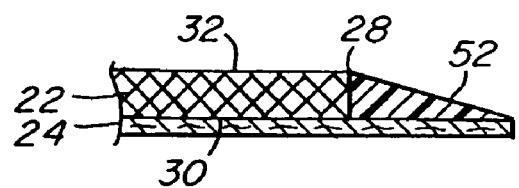
FIG. 9 is a cross-sectional view of the outer margin of a prosthesis in accordance with a further illustrative embodiment of the present invention.
Figure 10:
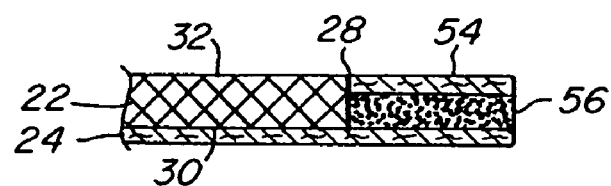
FIG. 10 is a cross-sectional view of the outer margin of a prosthesis in accordance with still another illustrative embodiment of the present invention.

Other illustrative embodiments for isolating the outer peripheral edge of the fabric are shown in FIGS. 8-10.

In FIG. 8, the interstices or openings along the outer margin 50 may be impregnated or otherwise occluded with a biocompatible material, such as silicone, polyethylene, polypropylene, urethane and the like, so as to inhibit tissue ingrowth that could lead to postoperative adhesions.

In FIG. 9, a body 52 of adhesion resistant material, such as a silicone, polyethylene, polypropylene, ePTFE, urethane and the like, may be deployed about the outer peripheral edge 28 of the repair fabric. Absorbable materials, such as SEPRAFILM available from Genzyme Corporation and oxidized, regenerated cellulose (Intercede (TC7)) may be employed for some applications. It is to be appreciated that any suitable adhesion resistant materials may be used as would be apparent to one of skill in the art.

In FIG. 10, a second barrier layer 54 may be placed along the outer margin of the second side of the repair fabric with the outer margin 56 of the fabric being melted and sealed between the first and second barrier layers.

It is to be understood, however, that the above embodiments are exemplary and any suitable peripheral barrier configuration may be implemented to isolate the outer peripheral edge of the fabric from developing adhesions to adjacent tissue and organs.

The present invention provides a prosthetic repair fabric having certain of the following advantages. The composite prosthesis combines the low adhesion incidence of a physical barrier over portions the repair fabric, including its outer peripheral edge, with desirable tissue ingrowth to the host tissue. The composite may be anchored in place by tissue ingrowth into the fabric interstices and/or may be sutured, stapled and the like to tissue.

It should be understood that the foregoing description of the invention is intended merely to be illustrative thereof and that other embodiments, modifications, and equivalents of the invention are within the scope of the invention recited in the claims appended hereto.

What is claimed is:

1. An implantable prosthesis for repairing a tissue or muscle wall defect, the implantable prosthesis comprising:
   a layer of repair fabric that is susceptible to the formation of adhesions with tissue and organs, the layer of repair fabric includes a plurality of tissue infiltratable interstices that are constructed and arranged to allow tissue ingrowth thereto, the layer of repair fabric including a first surface and an outer margin with an outer peripheral edge, the outer peripheral edge having a thickness, the outer margin of the layer of repair fabric having been melted and resolidified to substantially eliminate the tissue infiltratable interstices therein and render the entire thickness of the outer peripheral edge of the layer of repair fabric substantially impervious to tissue ingrowth so that the outer peripheral edge is resistant to the formation of adhesions with tissue and organs; and
   a barrier layer that inhibits tissue ingrowth and the formation of adhesions with tissue and organs thereto, the barrier layer being configured to inhibit the formation of adhesions between at least a portion of the first surface and adjacent tissue and organs.

2. The implantable prosthesis according to claim 1, wherein the outer margin has a non-uniform thickness.

3. The implantable prosthesis according to claim 2, wherein the outer margin has a thickness that decreases in an outward direction.

4. The implantable prosthesis according to claim 3, wherein the outer margin has a tapered shape.

5. The implantable prosthesis according to claim 1, wherein the layer of repair fabric includes an outer perimeter, the outer margin having been melted and resolidified along the entire outer perimeter.

6. The implantable prosthesis according to claim 5, wherein the barrier layer covers the entire first surface of the layer of repair fabric.

7. The implantable prosthesis according to claim 1, wherein the layer of repair fabric and the barrier layer are connected by at least one series of stitches.

8. The implantable prosthesis according to claim 7, wherein the series of stitches are formed from an adhesion resistant material.

9. The implantable prosthesis according to claim 7, wherein the series of stitches are disposed slightly inward of the outer peripheral edge.

10. The implantable prosthesis according to claim 1, wherein the layer of repair fabric is a knitted mesh.

11. The implantable prosthesis according to claim 10, wherein the knitted mesh is formed of polypropylene monofilament.

12. The implantable prosthesis according to claim 1, wherein the barrier layer is formed of ePTFE.

13. The implantable prosthesis according to claim 1, wherein a portion of the outer margin of the layer of repair fabric is fused to the barrier layer.

* * * * *